United States Patent [19]
Kocal et al.

[11] Patent Number: 5,763,728
[45] Date of Patent: Jun. 9, 1998

[54] RECOVERY AND RECYCLE OF HF-AMINE COMPLEX IN HF ALKYLATION

[75] Inventors: Joseph A. Kocal, Gurnee; Harold U. Hammershaimb, Western Springs; Robert J. Cornish, Carpentersville; Terry L. Marker, Warrenville; James F. Himes, Mount Prospect, all of Ill.

[73] Assignee: UOP, Des Plaines, Ill.

[21] Appl. No.: 533,038

[22] Filed: Sep. 25, 1995

Related U.S. Application Data

[63] Continuation-in-part of Ser. No. 174,857, Dec. 29, 1993, abandoned.

[51] Int. Cl.[6] .............................. C07C 2/58; C07C 2/56; C07C 7/00
[52] U.S. Cl. .................... 585/724; 585/719; 585/723; 585/730; 585/802
[58] Field of Search ........................... 585/719, 723, 585/724, 730, 802

[56] References Cited

U.S. PATENT DOCUMENTS

| | | | |
|---|---|---|---|
| 3,793,394 | 2/1974 | Chapman | 260/683.48 |
| 3,959,402 | 5/1976 | Mikulicz et al. | 260/683.48 |
| 5,073,674 | 12/1991 | Olah | 585/725 |
| 5,191,150 | 3/1993 | Child et al. | 585/809 |
| 5,237,122 | 8/1993 | Eastman et al. | 585/709 |

FOREIGN PATENT DOCUMENTS

| | | | |
|---|---|---|---|
| 243923A1 | 7/1985 | German Dem. Rep. | |
| 5792502 | 2/1982 | Japan | C01B 7/19 |

*Primary Examiner*—Glenn Caldarola
*Assistant Examiner*—Tanaga Anne Boozer
*Attorney, Agent, or Firm*—Thomas K. McBride; Eugene I. Snyder; Michael A. Moore

[57] ABSTRACT

An HF-agent complex, such as HF-pyridine complex where the complexing agent is pyridine, is recovered and recycled from a by-product containing stream in an alkylation process using the complex by (a) selectively removing a portion of the HF from the by-product stream to produce an HF-depleted stream having a molar ratio of HF per Lewis base site of the complexing agent of 3:1 to 5:1, (b) separating the resulting HF-depleted stream into a hydrocarbon phase enriched in ASO and an acid phase depleted in ASO and containing a substantial portion of the complex, and (c) recycling the acid phase to the hydrocarbon alkylation step.

11 Claims, 2 Drawing Sheets

RECOVERY AND RECYCLE OF HF-AMINE COMPLEX IN HF ALKYLATION

CROSS REFERENCE TO RELATED APPLICATION

This application is a continuation-in-part of application Ser. No. 08/174,857, filed Dec. 29, 1993 now abandoned, the contents of which are incorporated herein by reference thereto.

FIELD OF THE INVENTION

The field of the present invention is hydrocarbon processing. The invention generally relates to catalytic alkylation of hydrocarbons employing a liquid hydrogen fluoride (HF)-agent complex in a mixture, where the complexing agent contains a Lewis base site containing a Group 5A element. The invention specifically relates to catalytic alkylation of hydrocarbons employing a liquid HF-pyridine complex in a mixture.

BACKGROUND OF THE INVENTION

Alkylation using HF is a widely used commercial refining and petrochemical process. Generally, alkylation is the addition of an alkyl group to another hydrocarbon. Commercially, HF is used to alkylate isobutane with propylene, butylene, and amylene isomers to produce high octane gasoline blending components, as well as to alkylate benzene in the manufacture of detergents.

Because HF is volatile and the environmental risks arising from an accidental release of HF to the atmosphere are more and more undesirable, methods are sought to minimize the volatility of HF catalyst systems. One such method is to complex HF with suitable compounds that reduce the vapor pressure of HF and the tendency of the HF to form an aerosol.

Certain nitrogen-containing compounds, such as pyridine, picolines, quinoline, trimethylamine, and triethylamine, are known to form complexes with HF and to reduce its volatility. For example, see Japanese Patent Disclosure No. 57 (1982)-92502 (Oda et al). U.S. Pat. No. 5,073,674 (Olah) disclosed that mixtures of HF and preferred nitrogen-containing compounds (complexing agents) such as ammonia, methylamines, ethylamines, propylamines, butylamines, pentylamines, pyridine, picolines, melamine, and hexamethylene-tetramine remained effective catalysts in alkylation of alkanes by alkenes. Mixtures of Olah's preferred complexing agents with HF are hereinafter referred to as HF-amine complexes.

Such HF-amine mixtures are not suitable for economical use in prior art alkylation processes that use HF, however, because of the cost of adding fresh complexing agent as make-up. The prior art processes tend to concentrate the complexing agent in a stream that is rejected from the process. This happens because ASO, or acid-soluble oil, is soluble in the HF-amine complexes. ASO is a recognized term in the art of alkylation, and is sometimes referred to as HF-soluble oil, polymer, conjunct polymer, or polymer by-product. ASO is soluble in HF. In alkylation processes, ASO is an alkylation by-product that is generally formed by oligomerization of reactants or by reactions of impurities in the charge stock to the alkylation process. As such, ASO may have a variety of different compositions and physical properties depending on the reactants charged to the alkylation process, the operating conditions, etc. ASO is formed in both a motor fuel alkylation process and a detergent alkylation process. ASO may be in the boiling range of 149° to 482° C. (300° to 900° F.). It may also contain other non-hydrocarbon elements, including halogens, oxygen, nitrogen, sulfur, etc. As those skilled in the art of HF alkylation are aware, ASO generally decreases the activity of the HF catalyst. This effect can be beneficial at relatively low concentrations of ASO, but at higher concentrations it has an overall detrimental effect on the process. Therefore, in those processes where ASO is formed, ASO must be removed at least periodically from the circulating HF by a process that is commonly referred to as regeneration. In a typical HF-alkylation process, regeneration typically includes distilling or stripping HF from a stream of HF and ASO, returning the HF to the alkylation process, and rejecting the ASO. But, because HF-amine complexes typically have boiling points within the boiling range of ASO, complexing agent exits the process with the ASO and consequently the amount of complexing agent in the process is depleted. This ultimately results either in an increase in the volatility of the circulating HF stream, which may increase the potential for flash atomization, or else a requirement to add fresh complexing agent into the process as make-up, which may be uneconomical. Thus, there is a need for a method of separating the complexing agent from the ASO, so the separated complexing agent can be efficiently and economically recycled within the process.

U.S. Pat. No. 3,959,402 (Mikulicz et al.) discloses a method of recovering HF from a stream containing ASO, dissolved HF, and an azeotropic mixture of HF and water. The method comprises first stripping the stream to remove at least some of the HF, and then separating the HF-depleted stream into a CBM-rich phase and an ASO-rich phase.

U.S. Pat. No. 5,073,674 (Olah) discloses a process of alkylating aliphatic hydrocarbons with alkenyl hydrocarbons in the presence of liquid HF-ammonia or HF-amine complexes. The complexes preferably contain 70 to 95 wt-% HF, with 5 to 30 wt-% amine component. Therefore, the lowest molar ratio of HF per amine that Olah discloses is 2:1, which corresponds to a complex containing 70 wt-% HF and 30 wt-% ammonia. In Olah, after a predetermined period of time of stirring the hydrocarbons and the complex, the alkylation reaction mixture is depressured, and the hydrocarbon alkylate is subjected to a workup involving an alkaline wash. Olah omits describing the separation of the alkylation reaction mixture into a hydrocarbon stream and an acid stream, the presence of acid soluble oil (ASO) byproduct and complex in the acid stream, and the recovery of the complex from the acid stream.

East German Patent No. DD-243,923-A1 (Miethchen et al.) discloses a process for alkylating butenes with isobutenes in the presence of HF and amines or quaternary ammonium salts at a concentration of 70–100 milli-moles of amines or quaternary ammonium salts per kilogram of HF. The range of molar ratio of HF per amine that Miethchen et al. teaches is, therefore, about 500:1 to 700:1. The alkylation reactor effluent is passed to a settler from which are withdrawn a hydrocarbon stream and an acid stream that is recycled to the alkylation reactor. Miethchen et al. omits describing the presence of acid soluble oil (ASO) by-product and amine in the acid stream, and the recovery of the amines from the acid stream.

U.S. Pat. No. 3,793,394 (Chapman) discloses a process for the alkylation of olefins and isoparaffins in the presence of HF. Chapman, however, does not describe the presence of amines, and consequently Chapman describes the recovery of only HF, not the recovery of amines, from the alkylation reactor effluent. The alkylation reactor effluent is passed to a settler from which are withdrawn a hydrocarbon stream and an acid stream containing acid soluble oil (ASO) by-product. The acid stream is passed to an acid purification column in which hot isobutane strips HF from the acid stream, thereby producing an ASO stream containing 1910 pounds HF per 29 barrels ASO, or about 20 wt-% HF. The ASO stream is passed to an eductor in which hot isobutane strips more HF from the ASO stream, ultimately producing another ASO stream containing lower concentrations of HF, namely 8 pounds HF per 13.6 barrels ASO, or about 0.2 wt-% HF.

Japanese Patent Disclosure No. 57 (1982)-92502 (Oda et al.) discloses a method of vacuum distilling HF from HF-pyridine complexes having a molar ratio of HF per pyridine of between 3:1 and 20:1. On vacuum distillation, the complex liberates much of its HF, producing an HF-pyridine complex having an HF per pyridine molar ratio of 3:1. In order to reduce the HF per pyridine molar ratio below 3:1, Oda et al. found it necessary to react the 3:1 HF-pyridine complex with hydrogen chloride.

U.S. Pat. No. 5,191,150 (Child et al.) discloses a method of separating a stream containing ASO, HF, and sulfolane by first separating out HF and then gravitationally separating the HF-depleted stream into a polymer-rich stream and a sulfolane-rich stream.

U.S. Pat. No. 5,237,122 (Eastman et al.) discloses a method of separating a liquid containing HF and a sulfone compound by first adding water and then settling out an ASO phase and a sulfone-with-water phase.

BRIEF SUMMARY OF THE INVENTION

The present invention is a process for recovering an HF-agent complex from a hydrocarbon alkylation by-product stream containing acid soluble oil (ASO), HF, and HF-agent complex. The complexing agent contains a Lewis base site that comprises a Group 5A element, preferably nitrogen. The process first removes at least some of the HF from the by-product stream to form an HF-depleted stream, and then separates the HF-depleted stream into a phase enriched in ASO and another phase enriched in the HF-agent complex. This process is a particularly effective method of removing ASO from a mixture in which a Lewis base such as Olah's preferred complexing agents is used to reduce the tendency of HF to form an aerosol. This process can also be used to remove water that is present in the by-product stream.

The surprising discovery that has been made is that, in mixtures containing acid soluble oil (ASO), HF, and HF-agent complex, a reduction in the molar ratio of HF per Lewis base site of a complexing agent decreases the solubility of ASO in the HF-agent complex, despite the fact that ASO is very soluble in the agent. For example, a reduction in the molar ratio of HF per pyridine in a mixture containing ASO, HF, and HF-pyridine complex decreases the solubility of ASO in the HF-pyridine complex, despite the fact that ASO is very soluble in pyridine.

The manner in which HF associates with pyridine and like complexing agent and the properties that result from that association are unique. Thus, the present invention can be distinguished from prior art processes by the surprisingly different properties that a mixture of HF and complexing agent has in comparison to, say, a mixture of HF and water. On the one hand, ASO is not very soluble in water. Therefore, it is not surprising that, in a mixture of ASO, HF, and water, when the molar ratio of HF per water is reduced, an azeotropic mixture of HF and water is formed that is almost immiscible in ASO. On the other hand, ASO is very soluble in pyridine. Therefore, a person of ordinary skill in the art would expect that, in a mixture of ASO, HF, and pyridine, when the molar ratio of HF per pyridine is reduced, the remaining mixture of HF and pyridine would be miscible in ASO. Instead, and unexpectedly, it has been discovered that certain mixtures of HF and pyridine are almost immiscible in ASO. The present invention takes advantage of this surprising discovery about mixtures of HF and complexing agents such as pyridine to separate HF-agent complexes from ASO in a particularly effective and economical process. In processes that use HF and from which ASO is rejected at least intermittently, this invention may be used to separate, recover, and recycle the complexing agent before the ASO is disposed of. Therefore, this invention makes economical the use of pyridine and the like complexing agents to reduce the volatility of HF in processes that form ASO.

Accordingly, in a broad embodiment, this invention is a process for recovering and recycling a substantial portion of an HF-agent complex that is present in a by-product stream of a hydrocarbon alkylation process. The by-product stream contains by-product acid soluble oil (ASO), HF, and the HF-agent complex. The complexing agent contains at least one Lewis base site that contains a Group 5A element. The by-product stream has a molar ratio of HF per Lewis base site substantially above 5:1. A portion of the HF is selectively removed from the by-product stream to produce an HF-depleted stream having a molar ratio of HF per Lewis base site of 3:1 to 5:1. The HF-depleted stream is separated into a hydrocarbon phase enriched in ASO and an acid phase. The acid phase is depleted in ASO and contains a substantial portion of the HF-agent complex. The acid phase is recycled to the hydrocarbon alkylation step.

In a second embodiment, the invention is a process for recovering and recycling a substantial portion of an HF-pyridine complex that is present in a by-product stream of a hydrocarbon alkylation process. The by-product stream contains by-product acid soluble oil (ASO), HF, and the HF-pyridine complex. The by-product stream has a molar ratio of HF per pyridine above 17:1. A portion of the HF is selectively stripped from the by-product stream to produce an HF-stripped stream having a molar ratio of HF per pyridine of 6:1 to 17:1. A portion of the HF is selectively stripped from the HF-stripped stream to produce an HF-depleted stream having a molar ratio of HF per pyridine of 3:1 to 5:1. The HF-depleted stream is separated into a hydrocarbon phase enriched in ASO and an acid phase. The acid phase is depleted in ASO and contains a substantial portion of the HF-pyridine complex. The acid phase is recycled to the hydrocarbon alkylation step.

DETAILED DESCRIPTION OF THE INVENTION

Figure 1:
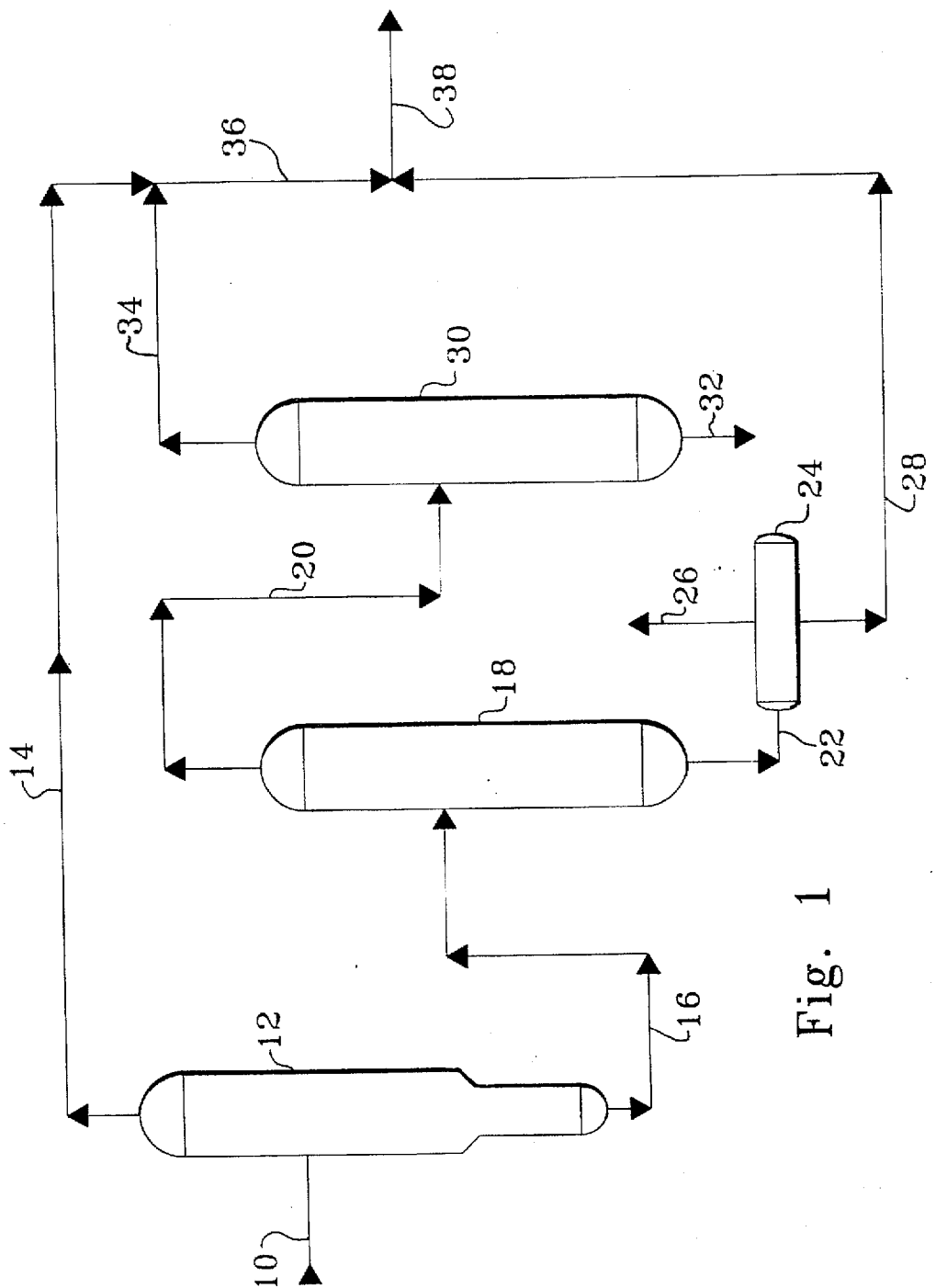
FIG. 1 is a simplified flow diagram of an embodiment of the invention.

The by-product stream charged to the subject process contains the by-product ASO, HF, and a complexing agent such as pyridine. The mixture may also contain water. The by-product stream may be produced by an HF alkylation process that is catalyzed by a mixture containing HF-agent complex.

The complexing agent contains a Lewis base site. Suitable Lewis bases that can function as complexing agents contain any one of the Group 5A elements, namely nitrogen, phosphorous, arsenic, antimony, and bismuth. When the molar ratio of HF per Lewis base site is reduced sufficiently, the HF-agent complex becomes sufficiently polar that it is not very soluble in ASO, which is generally non-polar. Thus, the HF-agent complex and ASO are then separable by phase separation. The more polar the HF-agent complex, the more facile is the separation between the HF-agent complex and the ASO.

The preferred Group 5A element is nitrogen. Within the group consisting of the Group 5A elements, the corresponding complexing agent generally becomes more polar as the molecular weight of the element decreases. This is because the electron cloud around the nucleus of the element becomes more localized and less diffuse as the molecular weight decreases. Therefore, the likelihood that the HF-agent complex will be sufficiently polar that the phase separation will be facile increases as the molecular weight of the Group 5A element decreases. For this reason, the preferred Group 5A element is that with the lowest molecular weight, namely nitrogen.

The complexing agents containing nitrogen can be: one of the chemical formula $NR_1R_2R_3$, where $R_1$, $R_2$, and $R_3$ can be alkyl, aryl or hydrogen, including ammonia, methylamine, ethylamine, propylamines, butylamines, pentylamines, dimethylamine, trimethylamine, diethylamine, triethylamine, diphenylamine, dibenzylamine, and aniline and alkyl- and aryl-substituted anilines including N,N-dimethylaniline; pyridine, and alkyl- and aryl-substituted pyridines, especially methyl-substituted pyridines, including picolines, lutidines, and collidine; a polycyclic compound, such as quinoline; a compound having more than one nitrogen atom, including noncyclic compounds such as ethylenediamine and cyclic compounds such as imidazoles and polyvinyl-pyridine; and a cyclic compound having other kinds of atoms such as oxygen in the ring, including morpholine. The complexing agent may contain more than one Lewis base site. Among the complexing agents containing nitrogen, the preferred complexing agent is a heterocyclic hydrocarbon compound having nitrogen in the ring as a heteroatom. The preferred complexing agent is pyridine. The by-product stream may contain more than one complexing agent.

In a mixture with HF, the Lewis base site may complex with HF to varying degrees. The tendency of Lewis bases to form complexes with HF is described in Japanese Patent Disclosure No. 57(1982)-92502 (Oda et al.), as well as in U.S. Pat. No. 5,073,674 (Olah). Although the extent of complexing depends on the type of Lewis base site and its amount in a mixture relative to the amount of HF, the exact degree to which a Lewis base site complexes with HF is uncertain. Oda et al. teaches that under certain conditions one pyridine molecule complexes with twenty HF molecules. As a working hypothesis, it is believed that the HF molecules that are in close proximity to the Lewis base site are more tightly complexed (e.g., by ionic inter-molecular forces), while HF molecules that are further from the Lewis base site are more loosely complexed (e.g., by Van der Waals forces). Oda et al. also teaches that under certain conditions one pyridine molecule forms a stable complex with three HF molecules. A mixture comprising HF and a complexing agent comprising a Lewis base site may be comprised of several HF-agent complexes, each having a different number of HF molecules per Lewis base site. Thus, it is to be understood that the term "HF-agent complex" refers to one or more HF-agent complexes. As a working hypothesis, it is believed that the extent to which the Lewis base site complexes with HF generally decreases as the molecular weight of the Group 5A element increases. Thus, HF will tend to complex more extensively with nitrogen-containing Lewis bases than with bismuth-containing Lewis bases. In any event, to the extent that the Lewis base site does complex with HF, the ease of phase separation of the complexing agent from the ASO may depend on the actual HF-agent complex that is present in the mixture, rather than on the Lewis base site itself.

In the present invention, the concentration of complexing agent in the by-product stream is generally between 1 and 50 wt-% on an ASO-free basis. The concentration of HF in the by-product stream is generally between 50 and 99 wt-% on an ASO-free basis. This typically corresponds to a molar ratio of HF per Lewis base site substantially in excess of 5:1. Within these broad ranges of complexing agent and HF concentrations lie various narrower ranges for particular complexing agents. For any particular complexing agent, its concentration in a by-product stream from an HF alkylation process will depend on factors that include its Lewis base site or sites, its physical properties, and its effect in vapor pressure suppression and in alkylation. For example, where the complexing agent is pyridine, the concentration of pyridine in the by-product stream is generally from 5 wt-% to 25 wt-% on an ASO-free basis, and preferably from 10 wt-% to 19 wt-% on an ASO-free basis. Accordingly, for the pyridine case, the concentration of HF in the by-product stream is generally from 75 wt-% to 95 wt-% on an ASO-free basis, and preferably from 81 wt-% to 90 wt-% on an ASO-free basis. Expressed in units of its molar ratio of HF per pyridine, the by-product stream is generally from 12:1 to 75:1 and preferably from 17:1 to 35:1.

This invention is preferably directed towards a stream containing an amine complexing agent, HF and ASO, with the most preferred amine complexing agent being pyridine. The following explanation is focused on the use of pyridine as a preferred embodiment of the present invention.

The concentration of ASO in the by-product stream is generally between 0.5 and 25 wt-%, but this is not a critical element of the invention. The particular composition of the ASO is not essential to the operation of this invention, and this invention is useful with any suitable ASO as described above. The operating conditions of this invention which are suitable for separation of ASO from a mixture containing ASO, HF and pyridine will depend on the ASO. Without undue experimentation, one skilled in the art can determine operating conditions that are suitable for different ASO compositions. It is not intended to limit the scope of this invention to any particular ASO composition.

In an HF alkylation process, water may enter the process with the hydrocarbons and then dissolve in the HF. Thus, water may be present in the by-product stream. The concentration of water in the by-product stream is generally between 0.1 and 3.0 wt-% on an ASO-free basis.

In accord with this invention, first at least a portion of the HF in the by-product stream is removed. The particular method of removing the HF from the by-product stream is not an essential feature of this invention. The method may also have the effect of removing from the by-product stream some pyridine, perhaps complexed with HF. Generally, however, the method employed will remove HF in a greater proportion than pyridine. Although the method of removal may be flashing, distillation or extraction, the preferred method of removing HF from the by-product stream is by stripping. Stripping is especially preferred where the complexing agent has the chemical formula $NR_1R_2R_3$ and where at least one of the R groups is alkyl and the other two R groups are alkyl or hydrogen. A stripping scheme is shown in U.S. Pat. No. 3,249,650, in which a stream containing isobutane and other light hydrocarbons is introduced into the bottom of a stripping column, which those skilled in the art of alkylation commonly refer to as a regenerator or rerun column. Although the regenerator may comprise a flash chamber or a packed bed column, it is preferably a trayed column. The heat for the separation may be provided by a stab-in type or a kettle type reboiler in the regenerator, however the heat is preferably provided to the stripper via the stripping medium, which can provide at least most and preferably all of the heat input into the stripper. Alternatively, the by-product stream may be preheated. The stripping medium may be nitrogen, hydrogen, methane, ethane, propane, or any other non-reactive gas. For a motor fuel alkylation process, the stripping medium may contain pentane, but preferably it contains isobutane which is heated or superheated. For a detergent alkylation process, the stripping medium may contain benzene, but preferably no stripping medium is used. It is an essential feature that this HF separation step be operated to produce an HF-depleted stream containing an HF per complexing agent mole ratio of 3:1 to 5:1.

In the bottoms product of the stripping column, which is referred to herein as the HF-depleted stream, the concentration of HF is generally between 20 and 80 wt-% on an ASO-free basis. Where the complexing agent is pyridine, the concentration of HF in the HF-depleted stream is generally between 40 wt-% and 70 wt-% on an ASO-free basis, and preferably between 43 and 65 wt-% on an ASO-free basis. Within these ranges, the lower the concentration of HF, the more facile is the subsequent separation of the HF-pyridine complex from the ASO, but the higher are the capital and operating costs of the stripping.

The process conditions under which HF is removed from the by-product stream include temperatures in the range of from 10° to 260° C. (50° to 500° F.), with 52° to 232° C. (125° to 450° F.) being preferred, and pressures in the range of from 138 to 1724 kPa (20 to 250 psi), with 586 to 1379 kPa (85 to 200 psi) being preferred.

The stripping column bottoms product contains HF-pyridine complex. Without undue experimentation, a person of ordinary skill in the art can determine the operating conditions of the stripping column that will not destroy the HF-pyridine complex. By "destroying" the HF-pyridine complex, it is meant the termination of interaction between HF and pyridine molecules that produces a complex, as evidenced by the properties of complexes described in Olah and Oda et al. In other words, when the HF-pyridine complex is destroyed, either the HF and the nitrogen of the pyridine interact and exhibit the properties of an ammonium fluoride salt, or the HF and the pyridine do not interact and each exhibits its properties as a pure substance.

Figure 2:
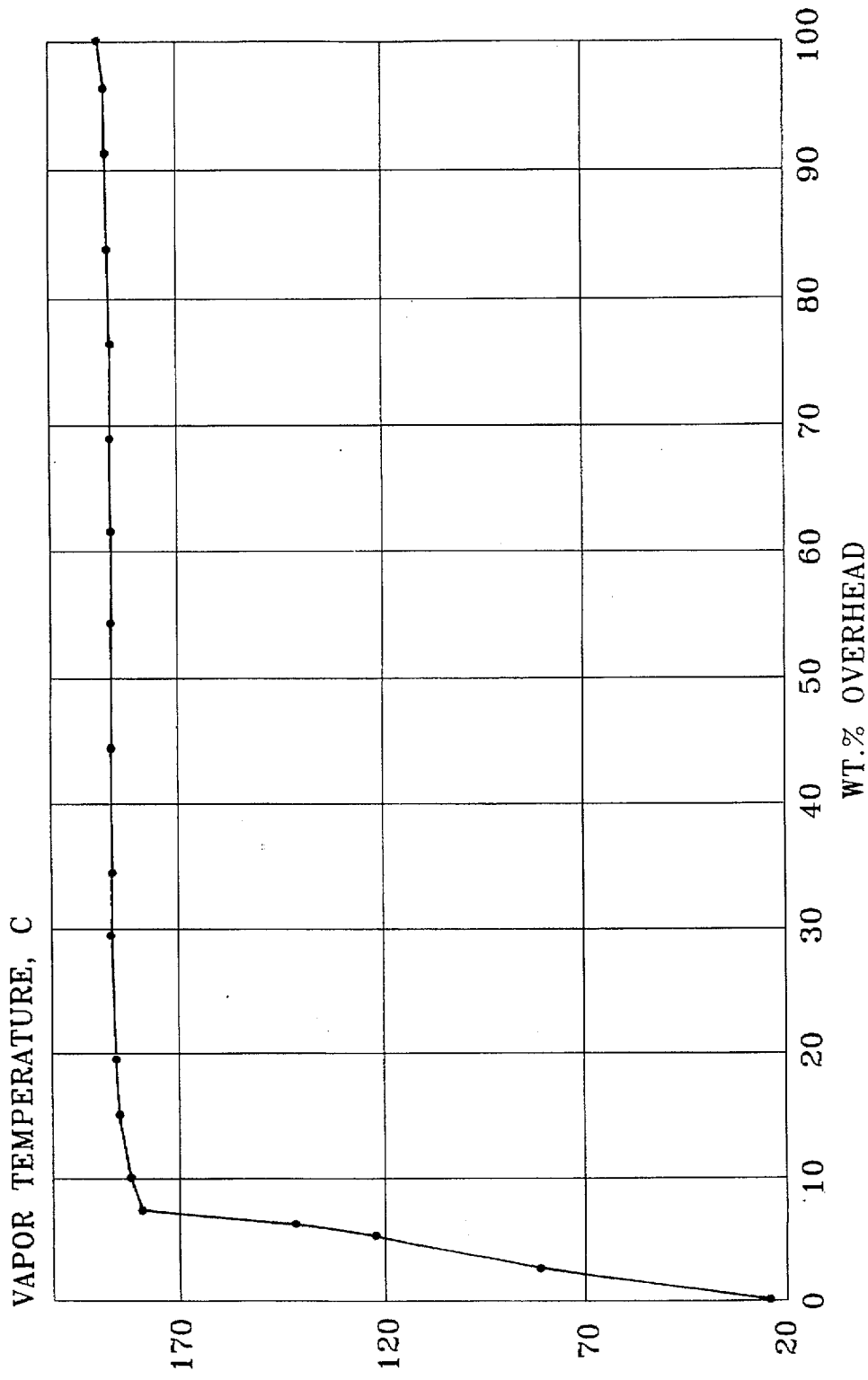
FIG. 2 shows the distillation curve of the batch atmospheric distillation of an HF-pyridine mixture having an initial molar ratio of HF per pyridine of 3.9:1. The vertical axis depicts the temperature of the overhead vapor and the horizontal axis depicts the percentage of the initial mixture that is distilled overhead.

A mere reduction in the molar ratio of HF per pyridine of a stream containing an HF-pyridine complex does not necessarily destroy the complex. Thus, the fact that the molar ratio of HF per pyridine of the stripping column bottoms product is less than the molar ratio of HF per pyridine of the HF-pyridine complex in the stripping column feed does not necessarily mean that the stripping destroyed the complex. For example, Japanese Patent Disclosure 57 (1982)-92502 (Oda et al.) discloses that a vacuum distillate of a HF-pyridine complex having a molar ratio of between 3:1 and 20:1 liberates much of its HF, producing an HF-pyridine complex having a molar ratio of 3:1, but without destroying the complex. In addition, vapor pressure tests show that at 80° C. (176° F.) pure HF has a vapor pressure of approximately 4900 mm Hg whereas a mixture of HF and pyridine having a molar ratio of HF per pyridine of 6.7:1 has a vapor pressure of only 784 mm Hg. In order to exhibit such a dramatic reduction in vapor pressure, a large proportion of the HF in the 6.7:1 mixture must be complexed with the pyridine even at 80° C. (176° F.). Finally, FIG. 2 shows that an atmospheric distillation at 186° C. (367° F.) of a mixture of HF and pyridine having an initial molar ratio of HF per pyridine of 3.9:1 does not destroy the complex. As shown in FIG. 2, the first 10% or so of the mixture that distills overhead is HF that corresponds to a reduction in the molar ratio of HF per pyridine of the mixture from 3.9:1 to 3.0:1. Thereafter, the HF-pyridine complex having a molar ratio of HF per pyridine of 3:1 is distilled overhead, at a constant overhead vapor temperature of 186° C. (367° F.).

It is believed that temperature is an important but not the only operating variable that determines whether a processing step that reduces the molar ratio of HF per pyridine of an HF-pyridine complex destroys the complex. Although it may be possible to destroy the complex by the action of heat alone at extremely high temperature, it is believed that the temperatures to which the complex is exposed in the processing steps of this invention are insufficient to thermally destroy the complex, in the absence of other complex-destroying factors. An example of a complex-destroying factor is elemental iron, which can react with the complex, removing one or more fluoride atoms from the complex and producing iron fluorides. This reaction between elemental iron and the complex is accelerated by increased temperature. Consequently, the possibility of some destruction of the complex is greatest in the high-temperature, bottom sections of distillation or stripping columns. This possibility of destruction of the complex can be minimized by employing ironfree alloys such as monel as the materials of construction of the columns and by minimizing the bottoms temperature of the columns. Persons of ordinary skill in the art can determine without undue experimentation the appropriate ranges of other processing variables that will lower the distillation temperature that is necessary to achieve a desired molar ratio of HF per pyridine, without destroying the HF-pyridine complex. For example, a decrease in the operating pressure or an increase in the amount of stripping vapor, such as isobutane, will decrease the distillation temperature. In this way, a person of ordinary skill in the art can arrive at operating conditions for the stripping column that ensure that the stripping column bottoms product contains HF-pyridine complex.

The stripping column bottoms product, or HF-depleted stream, is passed into a zone for separating the ASO from the HF-pyridine complex. The preferred method of separation is gravity-settling. Gravity-settling can be accomplished in a variety of mechanical devices, but the simplest device employs a quiescent zone that allows the HF-depleted stream to separate by gravity difference into an ASO-enriched hydrocarbon phase and a HF-pyridine-complex-enriched acid phase. In an alkylation process, the ASO-enriched hydrocarbon phase is rejected from the process, and the HF-pyridine-complex-enriched acid phase is recycled to the reaction zone of the process.

In more general terms, the method of separating the ASO from an HF-agent complex depends on the particular complexing agent used and on the conditions of the first separation zone. Where the effluent stream is a liquid and the complexing agent is also a liquid, the method of separation would typically be gravity-settling as described above, but it may also comprise flashing, distillation, centrifugation, extraction, and any suitable method that separates on the basis of differences in density, miscibility, or both.

Generally, the concentration of complexing agent in the ASO-enriched hydrocarbon phase is between 0.1 and 5 wt-%, but preferably the concentration is between 0.1 and 1.0 wt-%. In an HF alkylation process employing pyridine, the lower the concentration of pyridine in the ASO-enriched phase, the lower is the quantity of pyridine that is lost from the process, because the ASO-enriched phase is generally rejected from the process. The concentration of pyridine in the ASO-enriched hydrocarbon phase is generally not controlled directly. Instead, it is usually determined indirectly by setting other operating variables such as the molar ratio of HF per pyridine of the stripping column bottoms product. Nevertheless, as mentioned above, the consequences of losing pyridine from an alkylation process may be an increase in the volatility of the circulating HF which may increase the potential for flash atomization, or an increase in the rate at which pyridine is made up to the process, which is costly. In this context, it is important to note that another important advantage of the present invention is that the concentration of pyridine in the ASO-enriched phase is relatively low.

Generally, the concentration of ASO in the HF-amine-complex-enriched acid phase is between 0.1 and 50 wt-%. Where the complexing agent is pyridine, the concentration of ASO in the HF-pyridine-complex-enriched phase is generally between 0.1 wt-% and 25 wt-%, and preferably the concentration is between 0.1 and 15 wt-%. In an HF alkylation process employing pyridine, the lower the concentration of ASO in the HF-pyridine-complex-enriched phase, the lower the amount of ASO that is recycled to the alkylation process. Reducing the concentration of ASO that is recycled to an HF alkylation process is desirable because this reduces the size of the acid regenerator and of stripping columns downstream of the acid regenerator, if any. Alternatively, for a given charge rate to a given size of acid regenerator, reducing the concentration of ASO that is recycled to an HF alkylation process is desirable because this reduces the concentration of ASO in the circulating HF, which allows higher complexing agent concentrations and greater flash suppression.

The process conditions under which the HF-depleted stream is separated into an ASO-enriched hydrocarbon phase and an HF-agent-complex-enriched acid phase include temperatures in the range of from −18° to 260° C. (0° to 500° F.) with 149° to 260° C. (300° to 500° F.) being preferred when the ASO has been formed in a detergent alkylation process. A temperature of 66 to 149° C. (150° to 300° F.) is preferred when the ASO has been formed in a motor fuel alkylation process. Pressures in the range of from 138 to 1724 kPa (20 to 250 psi), preferably with the pressure being sufficient to minimize or prevent vaporization and to maintain the streams in a liquid phase.

The concentration of ASO in the HF-pyridine-complex-enriched acid phase can be further reduced by stripping the HF-pyridine-complex-enriched acid phase again to remove more HF, and then separating by phase separation into two streams. One advantage of further lowering of the concentration of HF is that even more ASO can be separated from the HF-pyridine-complex-enriched acid phase. This improved separation does not come without cost, because additional stripping and gravity-settling steps add both capital and operating costs to the process. Depending on the design of the stripping and settling zones, and the number of zones, the concentration of ASO in the HF-pyridine-complex-enriched acid phase that results from successive stripping and settling can be reduced to levels below 1.0 wt-%. The process conditions at which HF is further stripped from the HF-pyridine-complex-enriched acid phase include temperatures in the range of from about 10° to 260° C. (50 to 500° F.), with 38° to 232° C. (100° to 450° F.) being preferred, and pressures in the range of from 138 to 1724 kPa (20 to 250 psi), with 586 to 862 kPa (85 to 125 psi) being preferred. In HF-alkylation processes, ASO is removed from the process on average at a rate that is equivalent to its rate of formation. The optimum concentration of ASO in the HF-pyridine-complex-enriched acid phase that is returned to the alkylation process depends on technical and economic factors, including the capacity and operating costs of the regenerator and the desired concentration of ASO in the alkylation process. In general, for any given rate of ASO production and concentration of ASO in the alkylation process, the higher the concentration of ASO in the HF-pyridine-complex-enriched acid phase that is returned to the process, the greater must be the feed rate to the regenerator. This is because the ASO that is returned to the alkylation process with the HF-pyridine-complex-enriched acid phase must ultimately be rejected by the regenerator. Thus, this invention is particularly advantageous for alkylation processes wherein the target ASO concentration is relatively low and the feed rate capacity of the regenerator is limited.

Another embodiment of the subject invention is useful when water is present in the by-product stream. In an HF alkylation process, high concentrations of water in the circulating acid are undesirable because of the potential for corrosion. Therefore, it is desirable to maintain the concentration of water at an acceptable level in the process. In the present invention, a substantial amount of water in the by-product stream may be removed using the separation zone that removes a portion of the HF from the by-product stream. As described above, this separation zone may be a stripping column, in which case the overhead stream would contain the HF removed from the by-product stream, as well as some or most of the water in the by-product stream. However, this separation zone may also be operated so that a significant portion of the water is not removed with the overhead stream. Thus, the stripping column bottoms product, or the HF-depleted stream, could contain a substantial amount of the water that entered the process in the by-product stream. The HF-depleted stream passes into a separation zone, such as a gravity-settling zone, that produces an ASO-enriched hydrocarbon phase and a HF-pyridine-complex-enriched acid phase that comprises most of the water that entered with the HF-depleted stream.

One embodiment of the present invention removes a substantial portion of the water in the HF-pyridine-complex-enriched phase. This is another surprising aspect of this invention, because one might have expected the water in the HF-pyridine-complex-enriched stream to form a pyridine-water azeotrope or a tertiary azeotrope of pyridine-HF-water. If either of these azeotropes had formed, then removing water from the process would have had the undesirable consequence of removing the pyridine, too. Instead, the formation of the pyridine-water azeotrope or the pyridine-HF-water azeotrope is not observed. The explanation for this is that the pyridine is sufficiently complexed with HF that it is unavailable to form an azeotrope with water.

Taking advantage of this phenomenon, a simple and effective method has been found to reduce the water concentration in the HF-pyridine-complex-enriched acid phase before it returns to the alkylation process. The HF-pyridine-complex-enriched acid phase may be passed at least intermittently into a stripping column to remove water. This column may be a reboiled distillation column, or it may be a column that employs a stripping stream such as isobutane to strip the water from the HF-pyridine-complex-enriched acid phase. It should be noted here again that stripping is especially preferred where the complexing agent has the chemical formula $NR_1R_2R_3$ and where at least one of the R groups is alkyl and the other two R groups are alkyl or hydrogen. The heat required for the separation may be provided by a reboiler, or some or all of it may be provided by the stream used for stripping. Alternatively, some of the heat for the separation may be provided by preheating the HF-pyridine-complex-enriched acid phase before it enters the stripping column. Although a person of ordinary skill in the art would have expected such a column to produce either an overhead stream containing pyridine and significant water in the form of a pyridine-water azeotrope or a bottoms stream containing significant water in the form of a pyridine-HF-water azeotrope, the stripping column produces an overhead stream that contains HF and water but very little pyridine and a bottoms stream that contains significant pyridine but very little water. The water concentration of the overhead stream is generally from 5 wt-% to 15 wt-% and is preferably 10 wt-%.

The process conditions under which water is removed from the HF-pyridine-complex-enriched acid phase include temperatures in the range of from 10° to 260° C. (50° to 500° F.), with 38° to 232° C. (100° to 450° F.) being preferred. Pressures should be in the range of from 138 to 1742 kPa (20 to 250 psi), with 586 to 852 kPa (85 to 125 psi) being preferred.

The bottoms stream of this $H_2O$ stripping column is generally returned to the alkylation process, although if the bottoms stream contains significant ASO it may be sent to phase separation to remove ASO and then the ASO-depleted bottoms stream would be returned to the alkylation process. The overhead stream may be rejected at least intermittently from the process and sent directly to neutralization. Alternatively, the overhead stream can be sent to an additional separation zone which removes HF overhead for return to the alkylation process and produces a bottoms product comprising an azeotropic mixture of HF and $H_2O$ that is rejected from the process and sent to neutralization. Such an additional separation zone significantly reduces the loss of HF to neutralization. This additional separation zone may be a stripping column to remove HF. This column may be a reboiled distillation column, or it may be a column that employs a stripping stream such as isobutane. The function of this stripping column is to strip HF from the overhead stream that contains HF and water. The heat required for the separation may be provided by a reboiler, or some or all of it may be provided by the stream used for stripping. Alternatively, the heat for separation may be provided by preheating the overhead stream before it enters the column. Thus, this reduced loss of HF does not come without cost, because the additional stripping step adds both capital and operating costs to the process. But depending on the frequency of water removal, the amount of water removed, and the costs of neutralization and byproduct disposal, the use of a stripping column may be economically justifiable. Where an additional stripping zone is used to strip HF, the concentration of water on a hydrocarbon-free basis in the HF stream that is returned to the alkylation process is between 0.1 and 5 wt-% water, and preferably it is between 0.1 and 1 wt-% water.

The process conditions under which HF is removed from the $HF/H_2O$ overhead stream include temperatures in the range of from 38° to 260° C. (100° to 500° F.), with 49° to 232° C. (120° to 450° F.) being preferred. Pressures should be in the range of from 138 to 1724 kPa (20 to 250 psi), with 586 to 862 kPa (85 to 125 psi) being preferred.

Referring now to a preferred embodiment shown in FIG. 1, a by-product stream from an alkylation process, containing HF, an HF-pyridine complex, ASO, and water is charged in line 10 into a first stripper 12. In the first stripper 12, HF is selectively removed from the by-product stream in an overhead stream through lines 14 and 36, and returns to the alkylation process through a line 38. The bottoms stream of the first stripper is depleted in HF and is passed through a line 16 into a second stripper 18. In the second stripper 18, HF is selectively removed from the bottoms stream of the first stripper under conditions selected to result in a mole ratio of HF per complexing agent of 3:1 to 5:1. The bottoms stream of the second stripper is passed through a line 22 into a gravity settler 24. In the gravity settler, the bottoms stream of the second stripper separates by phase separation into a settler overhead phase enriched in ASO and a settler bottoms phase enriched in the complex. The settler overhead phase is passed through a line 26 to facilities that neutralize and dispose of the ASO. The settler bottoms phase is passed through a line 28 and returns to the alkylation process through the line 38. The overhead stream of the second stripper which contains both HF and water passes through a line 20 into a third stripper 30. In the third stripper 30, water is selectively removed from the overhead stream of the second stripper. The bottoms stream of the third stripper 30 is enriched in water and is passed through a line 32 to facilities that neutralize the HF and dispose of the water. The overhead stream of the third stripper 30 is enriched in HF, passes through a line 34 and the line 36, and returns to the alkylation process through the line 38.

EXAMPLE 1

This example shows the high degree of separation of ASO and HF-pyridine complex that can be achieved as a result of reducing the HF content of a mixture containing HF, pyridine, and ASO. A mixture containing HF-pyridine complex and ASO was subjected to HF stripping and then separated into a first ASO-rich phase and a first complex-rich phase. The first complex-rich phase contained 50.3 wt-% HF, had an HF-to-pyridine molar ratio of 5 and contained about 9.7 to 10.5 wt. % ASO. The first ASO-rich phase contained 0.12 to 0.5 wt-% pyridine (after neutralization) and 3.2 to 3.3 wt-% HF. Then, the first complex-rich phase was subjected to HF stripping again and separated into a second ASO-rich phase and a second complex-rich phase. The second complex-rich phase contained 42.9 wt-% HF, had an HF-to-pyridine molar ratio of 3, and contained less than 1.0 wt. % ASO. The second ASO-rich phase contained about 0.3 wt-% pyridine (after neutralization) and about 0.5 wt-% HF.

Thus, an alkylation catalyst containing HF, ASO and pyridine can be separated into a pyridine-rich stream containing less than about 1.0 wt-% ASO which can be returned to the alkylation process and an ASO-rich stream containing between 0.12–0.5 wt-% pyridine that can be rejected from the process.

EXAMPLE 2

This example shows that a pyridine-water azeotrope does not tend to form in an HF-pyridine-water mixture. A mixture of 140 g HF, 36 g water, and 79 g pyridine was distilled at atmospheric pressure. Two distinct temperatures were observed at which a constant boiling overhead temperature was maintained. The first was at 112° C., which corresponds to the boiling point of an azeotropic mixture of HF and H$_2$O and the second was at 182° C., which corresponds to the boiling point of the HF-pyridine complex that has an HF-to-pyridine molar ratio of 3.

EXAMPLE 3

Table 1 shows an example of the composition of some of the streams of the process shown in FIG. 1. This example is based on conventional engineering calculations and laboratory experiments. The molar ratio of HF per pyridine is between 20:1 and 21:1 in the by-product stream (line 10), 6:1 in the first stripper bottoms stream (line 16), and 3:1 in the second stripper bottoms stream (line 22). In the gravity settler 24, the second stripper bottoms stream is effectively separated into an overhead phase (line 26) that contains 99% ASO and is disposed of and a bottoms phase (line 28) that contains less than 1% ASO and returns to the alkylation process.

4. The process of claim 1 further characterized in that step (a) operates at a temperature of from 10° to 260° C. (50° to 500° F.) and at a pressure of from 138 to 1724 kPa (20 to 250 psi).

5. The process of claim 1 further characterized in that step (b) operates at a temperature of from −18° to 260° C. (0° to 500° F.) and a pressure of from 138 to 1724 kPa (20 to 250 psi).

6. The process of claim 1 wherein step (a) is performed in a stripping zone in which HF is selectively removed from the by-product stream by contacting such stream with isobutane to produce the HF-depleted stream.

7. The process of claim 1 further characterized in that the by-product stream contains H$_2$O which is removed therefrom in step (a) with the HF in an HF stream and subsequently separated at least in part from the HF stream by stripping in an H$_2$O separation column.

8. The process of claim 7 further characterized in that the H$_2$O separation column operates at a temperature of from 38° to 260° C. (100° to 500° F.) and at a pressure of from 138 to 1724 kPa (20 to 250 psi).

TABLE 1

| Composition in wt %: | Stream: | | | | | | | |
|---|---|---|---|---|---|---|---|---|
| | By-Product Stream 10 | First Stripper Bottoms 16 | Second Stripper Bottoms 22 | Settler Overhead 26 | Settler Bottoms 28 | Second Stripper Overhead 20 | Third Stripper Overhead 34 | Third Stripper Bottoms 32 |
| HF | 79 | 55 | 40 | <1 | 43 | 85 | 94 | 38 |
| Pyridine | 15 | 36 | 52 | 1 | 56 | 1 | <1 | 4 |
| ASO | 4 | 6 | 7 | 99 | <1 | 4 | 5 | 2 |
| Water | 2 | 3 | 1 | <1 | 1 | 10 | 1 | 57 |
| Total | 100 | 100 | 100 | 100 | 100 | 100 | 100 | 100 |

We claim:

1. A hydrocarbon alkylation process using an HF-agent complex and producing a by-product stream containing acid soluble oil (ASO), HF, and the HF-agent complex, wherein the complexing agent contains at least one Lewis base site containing a Group 5A element and the by-product stream has a molar ratio of HF per Lewis base site substantially above 5:1, further characterized in that a substantial portion of the HF-agent complex in the by-product stream is recovered and recycled to the hydrocarbon alkylation step by the steps of:

(a) selectively removing a portion of the HF from the by-product stream to produce an HF-depleted stream having a molar ratio of HF per Lewis base site of 3:1 to 5:1;

(b) separating the HF-depleted stream into a hydrocarbon phase enriched in ASO and an acid phase depleted in ASO and containing a substantial portion of the HF-agent complex; and (c) recycling the acid phase to the hydrocarbon alkylation step.

2. The process of claim 1 further characterized in that the HF-depleted stream contains HF at a concentration of not more than 80 wt % on an ASO-free basis.

3. The process of claim 1 further characterized in that the acid phase contains complexing agent at a concentration of not more than 5 wt % on an ASO-free basis.

9. The process of claim 1 wherein the complexing agent is a hetero cyclic hydrocarbon compound having nitrogen in the ring as a heteroatom.

10. The process of claim 9 wherein the hetero cyclic hydrocarbon compound is pyridine.

11. A hydrocarbon alkylation process using an HF-pyridine complex and producing a by-product stream containing acid soluble oil (ASO), HF, and the HF-pyridine complex, wherein the by-product stream has a molar ratio of HF per pyridine above 17:1, further characterized in that a substantial portion of the HF-pyridine complex in the by-product stream is recovered and recycled to the hydrocarbon alkylation step by the steps of:

(a) selectively stripping a portion of the HF from the by-product stream to produce an HF-stripped stream having a molar ratio of HF per pyridine of 6:1 to 17:1;

(b) selectively stripping a portion of the HF form the HF-stripped stream to produce an HF-depleted stream having a molar ratio of HF per pyridine of 3:1 to 5:1;

(c) separating the HF-depleted stream into a hydrocarbon phase enriched in ASO and an acid phase depleted in ASO and containing a substantial portion of the HF-pyridine complex; and (d) recycling the acid phase to the hydrocarbon alkylation step.

* * * * *